United States Patent [19]

Lin et al.

[11] Patent Number: 4,751,248

[45] Date of Patent: Jun. 14, 1988

[54] PREPARATION OF ALCOHOLS FROM SYNTHESIS GAS

[75] Inventors: Fan-Nan Lin; Filippo Pennella, both of Bartlesville, Okla.

[73] Assignee: Phillips Petroleum Company, Bartlesville, Okla.

[21] Appl. No.: 69,149

[22] Filed: Jul. 2, 1987

[51] Int. Cl.$^4$ .............................................. C07C 27/06
[52] U.S. Cl. .................................................. 518/707
[58] Field of Search ........................................ 518/707

[56] References Cited

U.S. PATENT DOCUMENTS

| | | | |
|---|---|---|---|
| 2,626,275 | 1/1953 | Sullivan | 260/440.6 |
| 2,750,430 | 6/1956 | Hagemann et al. | 260/638 |
| 3,598,527 | 8/1971 | Quartulli | 23/199 |
| 3,790,505 | 2/1974 | Casey et al. | 252/463 |
| 4,348,487 | 9/1982 | Goldstein et al. | 518/704 |
| 4,396,539 | 8/1983 | Sapienza et al. | 252/455 R |
| 4,403,044 | 9/1983 | Post et al. | 518/714 |
| 4,564,643 | 1/1986 | Shibata et al. | 518/717 |

OTHER PUBLICATIONS

K. Klier et al., "Catalytic Synthesis of Methanol from CO/H$_2$", Journal of Catalysis 74, 343–360 (1982).
H. H. Storch et al., "The Fischer–Tropsch and Related Syntheses", John Wiley & Sons, 1951, pp. 121, 349.

*Primary Examiner*—Howard T. Mars
*Attorney, Agent, or Firm*—K. K. Brandes

[57] ABSTRACT

A process for converting synthesis gas (CO+H$_2$) to aliphatic alcohols containing at least 2 carbon atoms comprises the steps of passing the synthesis gas first through a catalyst zone comprising (a) Co metal and/or Co oxide and (b) MgO and/or ZnO (preferably MgO), and then through a catalyst zone comprising (c) Cu metal and/or Cu oxide and (d) ZnO.

26 Claims, No Drawings

PREPARATION OF ALCOHOLS FROM SYNTHESIS GAS

BACKGROUND

This invention relates to the use of a new, effective catalyst system in a process for preparing alcohols from a mixture of carbon monoxide and hydrogen (synthesis gas). In another aspect, this invention relates to a process for producing higher aliphatic alcohols ($C_2+$ alcohols) from synthesis gas.

The catalytic production of saturated alcohols from mixtures of carbon monoxide and hydrogen is a well known technology. The primary objective of most of these processes is to produce methanol. More recently, however, higher alcohols having two or more carbon atoms per molecule have become increasingly valuable as fuels or as additives to gasoline. Thus there is a need for developing new, improved catalyst systems and employing them in processes for converting synthesis gas to alcohol products containing substantial amounts of $C_2+$ alcohols.

SUMMARY OF THE INVENTION

It is an object of this invention to produce aliphatic alcohols from a mixture of carbon monoxide and hydrogen (frequently referred to as synthesis gas) employing a new, effective catalyst system. It is a further object of this invention to catalytically convert carbon monoxide and hydrogen to linear and/or branched aliphatic alcohols, at a high selectivity to $C_2+$ alcohols. Other objects and advantages will become apparent from the detailed description and the appended claims.

In accordance with this invention, a process for converting synthesis gas to alcohols comprises the steps of
(A) passing a gas mixture comprising (preferably consisting essentially of) carbon monoxide and free hydrogen through a first catalyst zone comprising (preferably consisting essentially of) (a) cobalt metal or at least one compound of cobalt (preferably cobalt oxide) or a mixture of cobalt metal and at least one compound of cobalt, and (b) magnesium oxide (preferred) or zinc oxide or a mixture of magnesium oxide and zinc oxide; and
(B) passing the effluent from the first catalyst zone in step (A) through a second catalyst zone comprising (preferably consisting essentially of) (c) copper metal or at least one oxide of copper or a mixture of copper metal and at least one oxide of copper, and (d) zinc oxide;
wherein the contacting conditions in catalyst zones (A) and (B) are such as to obtain a product comprising at least one aliphatic alcohol (linear and/or branched) having at least 2 (preferably 2-8) carbon atoms per molecule.

In a preferred embodiment, the catalyst composition in the second catalyst zone further comprises (e) an inorganic refractory oxide support material (more preferably alumina). In a particularly preferred embodiment, the catalyst composition in the second catalyst zone consists essentially of components (c), (d) and (e).

DETAILED DESCRIPTION OF THE INVENTION

First Catalyst Zone

The catalyst composition in the first catalyst zone (hereinafter referred to as first catalyst composition) can contain any suitable relative amounts of components (a) and (b), as defined above. The weight percentage of (a) in the first catalyst composition is generally about 5–80 weight-%, preferably about 10–50 weight-%; and the weight percentage of (b) in the first catalyst composition is generally about 50–80 weight-%, preferably about 10–50 weight-%. Preferably, the first catalyst composition comprises (more preferably consists essentially of) (a) Co and/or CoO and (b) MgO.

Other ingredients and additives besides components (a) and (b) can also be present in the first catalyst composition, as long as their presence does not deleteriously affect the cooperative function of the two essential components (a) and (b). Such optional additives can be alumina, silica, aluminum phosphate titania, zirconia, clays, zeolites, alkali metal oxides or hydroxides and the like. These additives, if present, may comprise up to 30 weight-% of the entire first catalyst composition. Presently, however, the presence of these optional additives in the first catalyst composition is not preferred.

The first catalyst composition can be prepared in any suitable manner. In one preferred embodiment, the first catalyst composition is prepared by a process comprising the steps of coprecipitating at least one of carbonates, hydroxides and hydrated oxides (more preferably carbonates) of Co and of Mg (or, less preferably, Zn or mixtures of Mg and Zn in lieu of Mg alone) from aqueous solution containing dissolved compounds of Co and of Mg (or Zn or mixtures of Mg and Zn); then heating the formed coprecipitate (preferably after washing of the coprecipitate with water) at a first temperature so as to at least partially dry the coprecipitate (more preferably to reduce the water content to below 20 weight-% of the coprecipitate); and thereafter heating (i.e., calcining) the at least partially dried coprecipitate obtained in the previous step at a second temperature, which is higher than said first temperature, under such conditions as to substantially convert said at least partially dried coprecipitate obtained in the previous step to oxides of Co and of Mg (or, less preferably, Zn or mixtures of Mg and Zn).

The coprecipitating step can be carried out by adding an aqueous solution of a base (such as NaOH) or of a soluble alkali metal carbonate or bicarbonate or ammonium carbonate or bicarbonate to an aqueous solution containing soluble compounds of Co and of Mg (or Zn or mixtures of Mg and Zn) under suitable pH conditions (preferably at a pH of about 6–9). Any compounds of cobalt, magnesium and/or zinc that are substantially soluble in water can be employed, such as halides, nitrates, sulfates, bisulfates, carboxylates and the like. At present, the preferred compounds of Co and Mg are $Co(NO_3)_2$ and $Mg(NO_3)_2$, more preferably their hydrates (with about 6 moles of $H_2O$ per mole of nitrate). Any suitable concentration of the above-described compounds in each of the aqueous solutions can be employed so as to give the desired weight ratio or atomic ratio of Co to Mg and/or Zn. Preferred concentrations are described in Example I.

Preferably, the formed coprecipitate is separated from the aqueous phase, e.g., by filtration, centrifugation or any other suitable separation technique. Also preferably, the coprecipitate is washed with water and, optionally, thereafter with a water-soluble alcohol or with acetone.

The drying step can be carried under any suitable conditions, at atmospheric or vacuum conditions, preferably at a temperature of about 20°–150° C. The subsequent calcining step can be carried out at any suitable conditions in an inert or, preferably, oxidizing atmosphere (e.g., in air). Generally the calcining temperature is in the range of from about 150° to about 600° C. (preferably about 300° to 450° C.). The time of calcination is preferably in the range of from about 1 hour to about 20 hours.

Other, presently less preferred methods for preparing the first catalyst composition comprise impregnating support material comprising MgO or ZnO or both (preferably MgO alone) with a dissolved cobalt compound, drying the impregnated material (at drying conditions described above) and then calcining the dried material (at calcining conditions described above). Or a solution of a cobalt compound can be sprayed onto the support material defined above (preferably consisting essentially of MgO), followed by drying and calcining.

The finished first catalyst composition generally has a surface area (determined by BET/$N_2$ method; ASTM D3037) in the range of from about 10 to about 300 $m^2/g$, more preferably from about 20 to about 150 $m^2/g$. The material can, if desired, be ground and sieved so as to obtain a desired particle size range (preferably 10–80 mesh). The material can also be pelletized or compacted into various shapes (e.g., spherical, cylindrical, trilobal and the like). The first catalyst composition can be heated in the presence of a reducing gas, preferably in a free hydrogen containing gas at about 150°–500° C., preferably for about 1–20 hours, under such conditions as to at least partially reduce cobalt oxide to metallic cobalt. Preferably this reducing step is carried out before the catalyst composition is used in the conversion of synthesis gas to alcohols.

Second Catalyst Zone

The catalyst composition employed in the second catalyst zone (hereinafter referred to a second catalyst composition) comprises a mixture of (c) oxide of copper and/or copper metal and (d) zinc oxide. The second catalyst composition can be prepared by any suitable preparation technique. Preferably mixed oxides of Cu and Zn are prepared by coprecipitation of either the hydroxides of copper and zinc and/or the hydrated oxides of copper and zinc and/or the carbonates of copper and zinc, e.g. by addition of a base such as NaOH or a soluble carbonate such as $Na_2CO_3$, to an aqueous solution of copper and zinc salts such as nitrates, halides or sulfates of copper and zinc; at least partially drying of the formed coprecipitate; and then calcining (preferably in air) the coprecipitate under such conditions as to at least partially convert it to the oxides of copper and zinc. Drying and calcining conditions in the preparation of the second catalyst composition are substantially the same as described for the first catalyst composition. It is within the scope of this invention (yet presently less preferred) to impregnate zinc oxide with a copper compound (e.g., copper nitrate) and then calcine the thus impregnated material under such conditions as to convert the copper compound to CuO.

In a preferred embodiment, an inorganic refractory oxide material, such as alumina, silica, aluminosilicate (e.g., clay), titania, zirconia, chromia, magnesia, alumina phosphate, zirconium phosphate, mixtures of the above and the like, preferably alumina, is also present in said second catalyst composition. More preferably the second catalyst composition is prepared by either coprecipitation of hydroxides and/or hydrated oxides and/or carbonates of copper, zinc and aluminum and subsequent calcination under such conditions as to form the oxides of copper, zinc and aluminum; or by coprecipitation of hydroxides and/or carbonates of copper and zinc from an aqueous solution containing dispersed alumina, and subsequent calcination; or by the method described in U.S. Pat. No. 3,790,505, herein incorporated by reference. CuO-ZnO containing catalyst compositions are commercially available from United Catalysts, Inc., Louisville, Ky. and from BASF Wyandotte Corporation, Parsippany, N.J.

In a preferred embodiment, a CuO-ZnO containing catalyst composition used in the second catalyst zone is pretreated by heating with a reducing gas (e.g., $H_2$, CO), preferably a free hydrogen containing gas, so as to partially reduce CuO to $Cu_2O$ and/or Cu metal, before the catalyst composition is employed in the process of this invention. More preferably, said heating is carried out with a free hydrogen containing gas, most preferably a $H_2/N_2$ mixture at about 200°–500° C. for about 1–20 hours.

Preferably the weight ratio of Cu (present as metal and/or oxide) to Zn (present as oxide) in the second catalyst composition ranges from about 1:20 to about 20:1, more preferably from about 1:3 to about 3:1. If alumina ($Al_2O_3$) or another, less preferred inert refractory material (as defined above) is also present in said catalyst composition, the weight percentage of said inert material (preferably alumina) in the entire second catalyst composition can range from about 1 to about 90 weight-%, preferably from about 10 to about 70 weight-%. Generally the surface area (determined by the BET/$N_2$ method, ASTM D3037) of the second catalyst composition ranges from about 10 $m^2/g$ to about 300 $m^2/g$, preferably from about 20 $m^2/g$ to about 200 $m^2/g$.

Alcohol Synthesis

Any reactant mixture comprising chiefly carbon monoxide and free hydrogen gas (synthesis gas) can be employed in the alcohol synthesis process of this invention. Generally, operable reactants will contain about 5 to about 65 volume percent hydrogen, about 35 to about 95 volume percent carbon monoxide, about 0 to about 30 volume percent carbon dioxide, and about 0 to about 10 volume percent nitrogen. Preferred reactants will have a $H_2:CO$ volume ratio in the range of from about 1:2 to about 4:1, more preferably from about 1:1 to about 3:1. Reaction mixtures suitable for the process of this invention include commercially available synthesis gas. The reactant components, chiefly $H_2$ and CO, generally are in admixture when they are introduced into the reaction zone, where the contact with the catalyst compositions occurs.

However, it is possible (yet less preferred) to introduce a carbon monoxide containing gas and a free hydrogen containing gas separately into a suitable reactor and to mix the two feed streams, e.g., by static mixing means located in the reactor, so as to provide a mixture of hydrogen gas and carbon monoxide at the site of contact with the first catalyst compositions (described above).

Any suitable weight ratio of the first catalyst composition to the second catalyst composition can be employed. Generally this weight ratio is in the range of from about 0.2:1 to about 20:1, preferably in the range of from about 0.5:1 to about 10:1. More preferably the weight ratio of the first catalyst composition to the second catalyst composition is higher than 1:1, and most preferably is in the range of from about 1.1:1 to about 8:1.

Any suitable reactor or train of reactors that affords contact of the feed (reactant mixture) with the catalyst compositions contained in the first and second catalyst zones can be employed. Preferably, the catalyst compositions are confined in a stacked fixed bed in a heated reactor (generally tubular), and the reactant mixture passes through a layer of the first catalyst composition and then through a layer of the second catalyst composition at desired reaction conditions (either upflow or downflow). In another embodiment, the first catalyst composition is placed in a first reactor, and the second catalyst composition is placed in a second reactor in series. The process of this invention can be carried out as a batch process or, preferably, as a continuous process.

Typical contacting conditions to be employed in the synthesis reactions of the invention are well known. The following are merely suggested parameters from which the skilled artisan can extrapolate. Reaction conditions in both catalyst zones generally comprise a reaction temperature in the range of from about 200° C. to about 400° C., with about 250°-350°C. preferred; and a reaction pressure in the range of from about 300 to about 3000 psig, with about 500-1500 psig preferred. Other reaction variables such as flow rate of the gas feed mixture and catalyst volume may be selected in accordance with the particular reactants and reaction vessel involved. Generally, the gas hourly space velocity (GHSV) of the gas feed mixture is in the range of from about 500 to about 10,000 vol/vol/hour (volume of gas mixture per volume of catalyst composition per hour) at S.T.P. conditions (0° C., 1 atm).

The principal liquid products derived by the reaction of the instant process are straight chain and branched aliphatic alcohols. Generally, the chemical species produced will be saturated (aliphatic) alcohols containing from about 1 to about 10 carbon atoms. Non-limiting examples of formed aliphatic alcohols are methanol, ethanol, propanol, isopropanol, 1-butanol, 2-butanol, 2-methyl-1-propanol, n-pentanol, 2-pentanol, 3-pentanol, 2-methyl-1-butanol, 3-methyl-2-butanol, n- and isohexanols, n- and isoheptanols, n- and isooctanols, n- and isodecanols and the like, and mixtures thereof.

Higher aliphatic alcohols having 2-8 carbon atoms per molecule are the preferred products of the instant process. The presently more preferred alcohols are those having 2-6 carbon atoms per molecule. It is desirable that the selectivity of $C_2+$ alcohols be maintained at acceptably high levels. If one operates within the teachings of this invention, selectivities to alcohols containing two carbons or more per molecule will generally be above 20 percent, and be preferably about 30 percent to 60 percent.

The formed liquid product (mainly methanol and $C_2$-$C_8$ aliphatic alcohols) can be condensed and then separated into two or more fractions containing different alcohols. The separation can be carried out by any conventional technique such as fractionated distillation. Generally, a methanol fraction, an ethanol fraction, a $C_3$-$C_5$ alcohol fraction (useful as additive to gasoline) and a higher alcohol fraction ($C_5$-$C_8$) are obtained, and can be recovered as separate product streams. Gaseous reaction effluents, mainly unreacted hydrogen and carbon monoxide, can be utilized as fuel or can be recycled to the reactant(s) described above.

The following examples are presented in further illustration of the invention and are not to be considered as unduly limiting scope of this invention.

EXAMPLE I

This example illustrates the preparation of the catalysts used in the first and second catalyst zones.

Catalyst A (CoO/MgO) was prepared by dissolving 207.3 grams of $Co(NO_3)_2.6H_2O$ and 212.2 grams of $Mg(NO_3)_2.6H_2O$ in 650 cc of distilled water, heating this first solution (pH=3) to about 50° C., then dropwise adding the first solution to a second solution comprising 166.3 grams of $Na_2CO_3$ in 500 cc of distilled water having a temperature of about 60° C. and a pH of 12. The final mixture of the two solutions, which had a pH of 7.5, was filtered, and the filter cake of carbonates and/or oxides of Co and Mg was washed by slurring it in 900 cc of distilled water at 60° C. The slurry was filtered, and the filter cake was washed again five more times, as described above. The washed filter cake was dried under an IR heat lamp in a nitrogen atmosphere and then calcined for 12 hours at a temperature ranging from 220° C. to 350° C. Calcined Catalyst A was crushed and sieved. A 16/40 mesh fraction was recovered, which contained about 33 weight-% Co, about 16 weight-% Mg and about 3 weight-% Na, and had a BET/$N_2$ surface area of about 85 $m^2$/g.

Catalyst B (CoO/ZnO) was prepared substantially in accordance with the procedure for Catalyst A, except that $Zn(NO_3)_3.6H_2O$ was used in lieu of $Mg(NO_3)_2.6H_2O$. Catalyst B contained 32 weight-% Co, 25 weight-% Zn and 0.4 weight-% Na, and had a BET/$N_2$ surface area of 69 $m^2$/g.

Catalyst C (CuO/ZnO/$Al_2O_3$), prepared substantially in accordance with the procedure of Example I of U.S. Pat. No. 3,790,505, was supplied by United Catalysts, Inc., Louisville, KY. The material was crushed and sieved so as to obtain a 16/40 mesh fraction. Catalyst C contained about 35 weight-% Cu, about 35 weight-% Zn, about 4 weight-% Al (thus about 8 weight-% $Al_2O_3$) and about 4 weight-% graphite. The BET/$N_2$ surface area of Catalyst C was of about 40 $m^2$/g.

EXAMPLE II

This example illustrates the use of Catalysts A, B and C in the conversion of CO+$H_2$ (synthesis gas) to alcohols. All test runs were carried out using one and two catalyst layers, respectively, containing 5 cc of one of the catalyst compositions of Example I and 25 cc of 3 mm glass beads, placed in a 1" pipe stainless steel reactor, mounted vertically in a furnace equipped with temperature control. Synthesis gas feed passed in a downflow manner through the reactor. The product stream exited the reactor via a cold trap cooled to 0° C. The cold trap could be isolated and removed from the system for weighing, so as to determine the quantity of liquid that it contained. The liquid was weighed and sampled for analysis by gas liquid chromatography.

Table I summarized pertinent information of runs made with catalysts A and C, at comparable process conditions (temperature: 285°-320° C.; pressure: about 900 psig; gas hourly space velocity: about 2600 volume of feed/volume of catalyst/hour; $H_2$/CO volume ratio: about 1:1).

TABLE I

| Run | 1 (Invention) | 2 (Invention) | 3 (Control) | 4 (Control) | 5 (Control) |
|---|---|---|---|---|---|
| First Catalyst Layer | A | A | C | A | C |
| Second Catalyst Layer | C | C | A | None | None |
| Wt. Ratio of A:C | 2.7:1 | 0.6:1 | 3:1 | N/A | N/A |
| Temperature (°C.) | 285 | 285 | 285 | 285 | 288 |
| Yield of Organic Products (mg/g Catalyst/Hour) | 184 | 390 | 287 | 241 | 361 |
| Selectivity (Weight %) | | | | | |
| to Gaseous Hydrocarbons | 33 | 12 | 60 | 40 | 2 |
| to Methanol | 17 | 63 | 8 | 8 | 85 |
| to $C_2$-$C_6$ Alcohols | 40 | 15 | 7 | 25 | 10 |
| to $C_7$+ Alcohols | 3 | 2 | 1 | 4 | 1 |
| to Aldehydes | 0 | 0 | 11 | 12 | 0 |
| to Esters | 1 | 3 | 8 | 3 | 2 |
| to Liquid Hydrocarbons | 6 | 5 | 5 | 8 | 0 |
| Yield of Water (mg/g Catalyst/Hour) | 35 | 14 | 109 | 98 | 4 |

Test results in Table I show:

(a) Run 1 using a stacked bed with Catalyst A in the first catalyst layer (first catalyst zone) and Catalyst C in the second (i.e., subsequent) catalyst layer (second catalyst zone), wherein the amount of A was greater than the amount of C, yielded more of the desirable $C_2$-$C_6$ alcohol fraction than any of the other runs, including Run 4 with only Catalyst A and Run 5 with only Catalyst C. The above result is quite unexpected.

(b) Neither Run 1 nor Run 2 yielded undesirable aldehyde by-products. This result is quite unexpected because Run 4 with only Catalyst A yielded considerable amounts of aldehydes.

(c) Invention Run 1 using a greater weight ratio of A to C than invention Run 2 yielded more $C_2$-$C_6$ alcohols and is thus considered the preferred mode of this invention.

(d) Control Run 3 using Catalyst C in the first catalyst layer and Catalyst A in the second catalyst layer yielded considerably less $C_2$-$C_6$ alcohols and considerably more undesirable gases, aldehydes, esters and water than invention Runs 1 and 2 using Catalyst A in the first catalyst zone and Catalyst C in the second catalyst zone. The results of Run 3 makes the beneficial results of Runs 1 and 2 (higher $C_2$-$C_6$ alcohol yield; no aldehyde formation) even more unexpected and surprising.

The effect of the reaction temperature was investigated for the invention process using a stacked bed of Catalyst A in the first catalyst layer (catalyst zone) and Catalyst C in the second catalyst layer. Test results are summarized in Table II.

TABLE II

| Run | 1 (Invention) | 6 (Invention) | 7 (Invention) |
|---|---|---|---|
| First Catalyst layer | A | A | A |
| Second Catalyst layer | C | C | C |
| Wt. Ratio of A:C | 2.7:1 | 2.7:1 | 2.7:1 |
| Temperature (°C.) | 285 | 300 | 320 |
| Yield of Organic Products (mg/g Catalyst/Hour) | 184 | 226 | 536 |
| Selectivity (Wt. %): | | | |
| to Gaseous Hydrocarbons | 33 | 33 | 42 |
| to Methanol | 17 | 15 | 10 |
| to $C_2$-$C$ Alcohols | 40 | 38 | 34 |
| to $C_7$+ Alcohols | 3 | 4 | 1 |
| to Aldehydes | 0 | 0 | 0 |
| to Esters | 1 | 2 | 5 |
| to Liquid Hydrocarbons | 6 | 7 | 7 |
| Yield of Water (mg/g Catalyst/Hour) | 35 | 29 | 40 |

Test results in Table II indicate that at the above test conditions a higher reaction temperature resulted in enhanced overall product yield but in somewhat lower $C_2$-$C_6$ alcohol yield and slightly higher yield of ester by-products. At the present reaction conditions, a temperature of about 300°–310° C. is an optimal reaction temperature range (in terms of total product yield, yield of $C_2$-$C_6$ alcohols and yield of undesirable by-products). It is expected that the optimal temperature will be higher when flow rates of syngas are used that are higher than those in these test runs.

EXAMPLE III

In this example the preformance of Catalyst A in a syngas reaction is compared with that of Catalyst B. The experimental step was substantially the same as described in the first paragraph of Example II. Reaction conditions were: reaction temperature of 250° C., reaction pressure of 900 psig, gas hourly space velocity of about 2000 volume/volume catalyst/hour, and $H_2$/CO volume ratio of about 2:1. Test results are summarized in Table III.

TABLE III

| Run | 8 | 9 |
|---|---|---|
| Catalyst | A-7 | B |
| Yield of Organic Products (mg/g Catalyst/Hour) | 212 | 88 |
| Selectivity (Wt. %) | | |
| to Gaseous Hydrocarbons | 30 | 33 |
| to Methanol | 5 | 3 |
| to $C_2$-$C_7$ Alcohols | 28 | 18 |
| to Aldehydes | 20 | 25 |
| to Liquid Hydrocarbons | 17 | 21 |
| Yield of Water (mg/g Catalyst/Flow) | 178 | 38 |

Data in Table III show that Catalyst B (CoO/ZnO) is an active catalyst for the conversion of syngas to higher alcohols, but is not as active and selective to alcohols as Catalyst A. Based on these results, it is concluded that a CoO/ZnO catalyst composition can be used in the first catalyst zone of the process of this invention, but the CoO/MgO catalyst composition is more preferred than the CoO/ZnO catalyst composition.

Reasonable variations, modifications and adaptations for various usages and conditions can be made within the scope of the disclosure and the appended claims, without departing from the scope of this invention.

We claim:

1. A process for converting synthesis gas to alcohols comprising the steps of
   (A) passing a gas mixture comprising carbon monoxide and free hydrogen through a first catalyst zone comprising (a) cobalt metal or at least one compound of cobalt or a mixture thereof and (b) magnesium oxide or zinc oxide or a mixture thereof; and
   (B) passing the effluent from the first catalyst zone in step (A) through a second catalyst zone comprising (c) copper metal or at least one oxide of copper or a mixture thereof and (d) zinc oxide;
   wherein the contacting conditions in steps (A) and (B) are such as to obtain a product comprising at least one aliphatic alcohol having at least 2 carbon atoms per molecule.

2. A process in accordance with claim 1 wherein catalyst component (b) in said first catalyst zone is MgO.

3. A process in accordance with claim 1 wherein the weight percentage of component (a) of the catalyst composition in said first catalyst zone is in the range of from about 5 to about 80, and the weight percentage of component (b) of the catalyst composition in said first catalyst zone is in the range of from about 5 to about 80.

4. A process in accordance with claim 3 wherein said weight percentage of component (a) is in the range of from about 10 to about 50, and said weight percentage of component (b) is in the range of from about 10 to about 50.

5. A process in accordance with claim 1 wherein the weight ratio of Cu to Zn in the catalyst composition in said second catalyst zone is in the range of from about 1:20 to about 20:1.

6. A process in accordance with claim 5 wherein said weight ratio of Cu to Zn is in the range of from about 1:3 to about 3:1.

7. A process in accordance with claim 1 wherein the catalyst composition in said second catalyst zone further comprises (e) an inorganic refractory oxide material.

8. A process in accordance with claim 7 wherein said inorganic refractory oxide material is alumina.

9. A process in accordance with claim 7 wherein the weight percentage of said inorganic refractory oxide material in the catalyst composition in said second catalyst zone is in the range of from about 1 to about 90 weight-%.

10. A process in accordance with claim 7 wherein said inorganic refractory oxide material is alumina and the weight percentage of alumina in the catalyst composition in said second catalyst zone is in the range of from about 10 to about 70.

11. A process in accordance with claim 1 wherein the weight ratio of the catalyst composition in said first catalyst zone to the catalyst composition in said second catalyst zone is in the range of from about 0.2:1 to about 20:1.

12. A process in accordance with claim 11 wherein said weight ratio of the two catalyst compositions in the range of from about 0.5:1 to about 10:1.

13. A process in accordance with claim 11 wherein said weight ratio of the two catalyst compositions is in the range of from about 1.1:1 to about 8:1.

14. A process in accordance with claim 1 wherein the BET/$N_2$ surface area of the catalyst composition in said first catalyst zone is in the range of from about 20 to about 150 $m^2/g$, and the BET/$N_2$ surface area of the catalyst composition in said second catalyst zone is in the range of from about 20 to about 200 $m^2/g$.

15. A process in accordance with claim 1 wherein the catalyst composition in said first catalyst zone has been prepared by a process comprising the steps of (i) coprecipitating at least one of carbonates, hydroxides and hydrated oxides of Co and Mg; (ii) heating the coprecipitate formed in step (i) under such conditions as to at least partially dry said coprecipitate; and (iii) calcining the at least partially dried coprecipitate obtained in step (ii) under such conditions as to obtain oxides of Co and Mg.

16. A process in accordance with claim 15 wherein the preparation process additionally comprises the step of (iv) heating the calcined material obtained in step (iii) with a reducing gas under such conditions as to at least partially reduce cobalt oxide to cobalt metal.

17. A process in accordance with claim 1 wherein the catalyst composition in said second catalyst zone has been prepared by a process comprising the steps of (I) coprecipitating at least one of carbonates, hydroxides and hydrated oxides of Cu and Zn; (II) drying the coprecipitate formed in step (I) under such conditions as to at least partially dry the coprecipitate formed in step (I); and (III) calcining the at least partially dried coprecipitate obtained in step (II) under such conditions as to obtain oxides of Cu and Zn.

18. A process in accordance with claim 17 wherein the preparation process additionally comprises the step of (IV) heating the calcined material obtained in step (III) with a reducing gas under such conditions as to at least partially reduce CuO to at least one of $Cu_2O$ and Cu metal.

19. A process in accordance with claim 17 wherein the coprecipitate formed in step (I) additionally comprises at least one of carbonates, hydroxides and hydrated oxides of alumina; and the calcined material obtained in step (III) additionally comprises alumina.

20. A process in accordance with claim 1 wherein said gas mixture used in step (A) comprises about 5 to about 65 volume percent hydrogen and about 35 to about 95 volume percent carbon monoxide.

21. A process in accordance with claim 1 wherein the volume ratio of $H_2$:CO in said gas mixture is in the range of from about 1:2 to about 4:1.

22. A process in accordance with claim 21 wherein said contacting conditions in steps (A) and (B) comprise a reaction temperature in the range of from about 200° to about 400° C. and a reaction pressure in the range of from about 300 to about 3000 psig.

23. A process in accordance with claim 22 wherein said reaction temperature is about 250°–350° C. and said reaction pressure is about 500–1500 psig.

24. A process in accordance with claim 22 wherein said contacting conditions further comprise a gas hourly space velocity of said gas mixture in the range of from about 500 to about 10,000 volume gas mixture/volume catalyst composition/hour.

25. A process in accordance with claim 1 wherein said product comprises aliphatic alcohols containing 2–8 carbon atoms per molecule.

26. A process in accordance with claim 1 further comprising the step of
   (C) separating the product which contains a plurality of alcohols into at least two liquid fractions comprising different alcohols.

* * * * *